(12) United States Patent
Furuya et al.

(10) Patent No.: US 11,549,885 B2
(45) Date of Patent: Jan. 10, 2023

(54) OPTICAL CHEMICAL ANALYSIS APPARATUS

(71) Applicant: Asahi Kasei Microdevices Corporation, Tokyo (JP)

(72) Inventors: Takaaki Furuya, Tokyo (JP); Toshiro Sakamoto, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 17/448,380

(22) Filed: Sep. 22, 2021

(65) Prior Publication Data

US 2022/0091025 A1 Mar. 24, 2022

(30) Foreign Application Priority Data

Sep. 24, 2020 (JP) .............................. JP2020-160120

(51) Int. Cl.
*G02B 6/42* (2006.01)
*G01N 21/3504* (2014.01)
*G01N 33/00* (2006.01)

(52) U.S. Cl.
CPC ....... *G01N 21/3504* (2013.01); *G01N 33/004* (2013.01); *G02B 6/4206* (2013.01); *G02B 6/4298* (2013.01); *G01N 2201/062* (2013.01); *G01N 2201/0634* (2013.01)

(58) Field of Classification Search
CPC ............................ G02B 6/4298; G02B 6/4206
See application file for complete search history.

(56) References Cited

U.S. PATENT DOCUMENTS

| | | | |
|---|---|---|---|
| 7,194,166 B1 | 3/2007 | Gunn, III | |
| 2015/0309261 A1* | 10/2015 | Kobyakov | ............. G02B 6/124 385/14 |
| 2018/0074271 A1* | 3/2018 | Song | ................... G02B 6/4206 |
| 2019/0310418 A1 | 10/2019 | Karimelahi et al. | |
| 2020/0116631 A1 | 4/2020 | Sakamoto et al. | |

FOREIGN PATENT DOCUMENTS

| | | |
|---|---|---|
| JP | 2005300212 A | 10/2005 |
| JP | 2018146568 A | 9/2018 |
| JP | 2019100770 A | 6/2019 |
| JP | 2020056685 A | 4/2020 |
| WO | 2018179752 A1 | 10/2018 |

* cited by examiner

*Primary Examiner* — Sung H Pak
(74) *Attorney, Agent, or Firm* — Kenja IP Law PC

(57) ABSTRACT

An optical chemical analysis apparatus (14) includes an optical waveguide (15) and a light source (17). The optical waveguide (15) has a core layer (12) that includes a light propagator (10), through which light can propagate in an extension direction, and a diffraction grating (first diffraction grating (11)) that connects optically to the light propagator (10). The light source (17) is configured to inject the light into the diffraction grating by emitting incoherent light. The diffraction grating further includes a light intake region for introduction of light from the light source, and the light source includes at least one light emitting point at a position such that the difference between the shortest optical distance Lab to the light intake region and the longest optical distance Lac to the light intake region is less than half of the wavelength, in a vacuum, of the light.

18 Claims, 9 Drawing Sheets

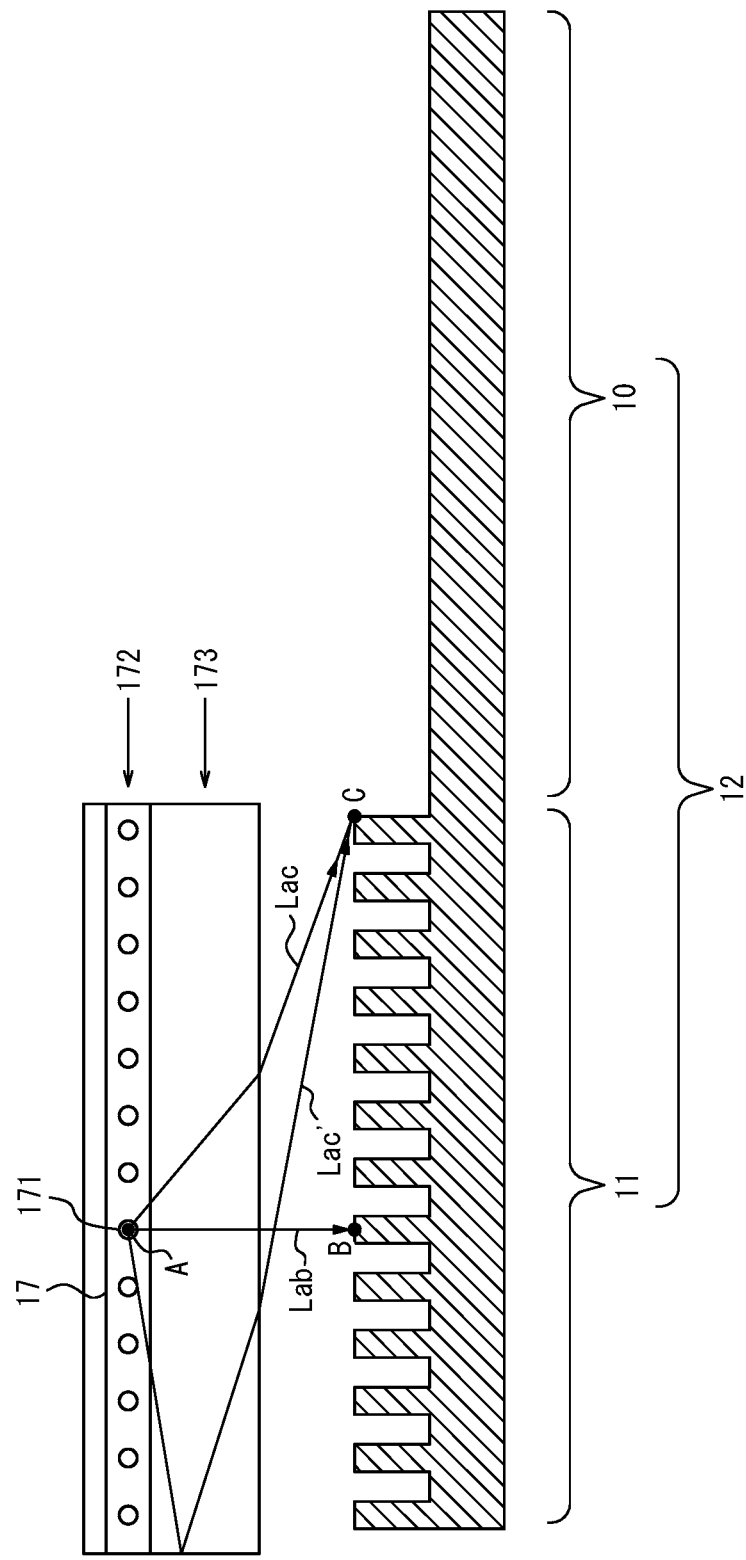

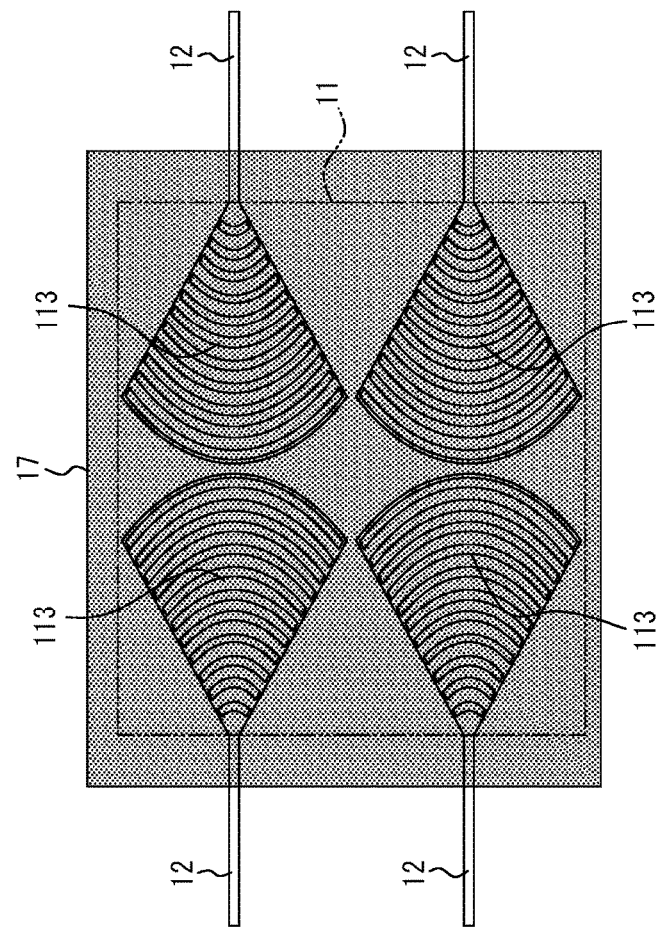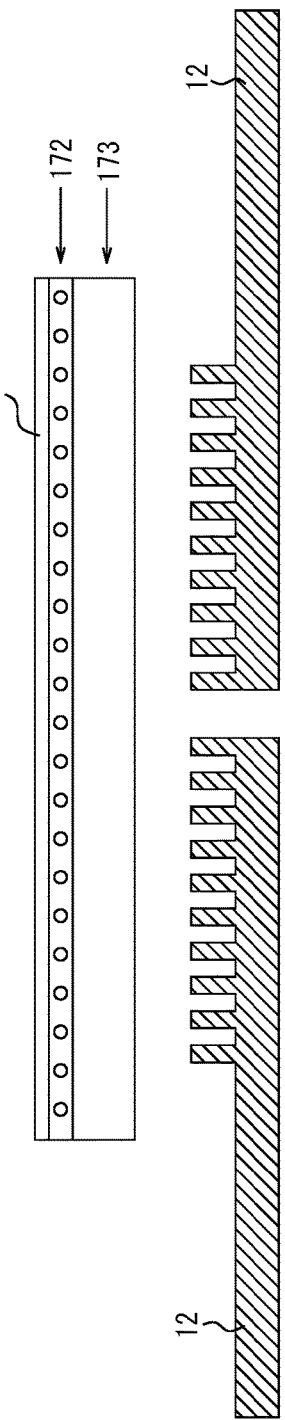

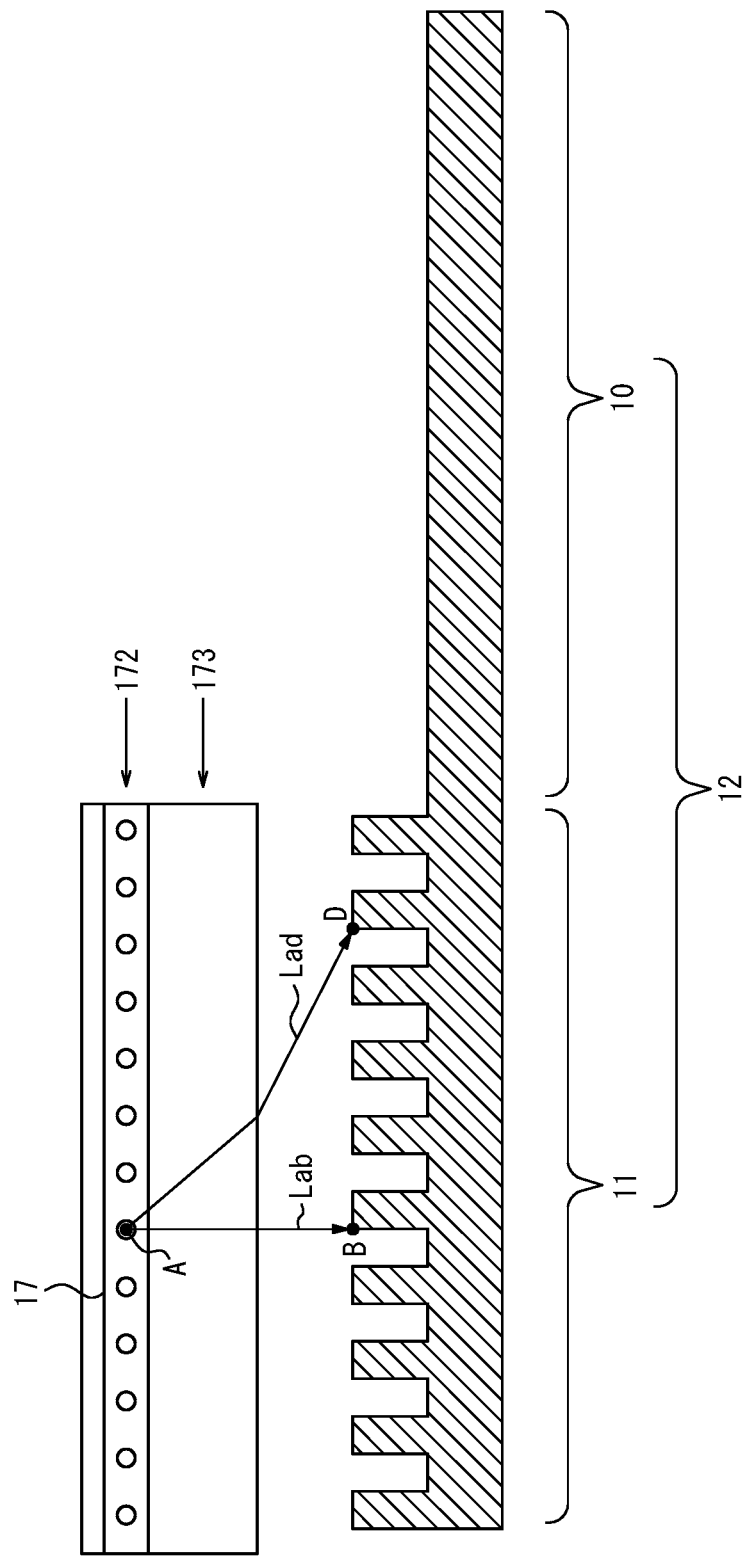

FIG. 8
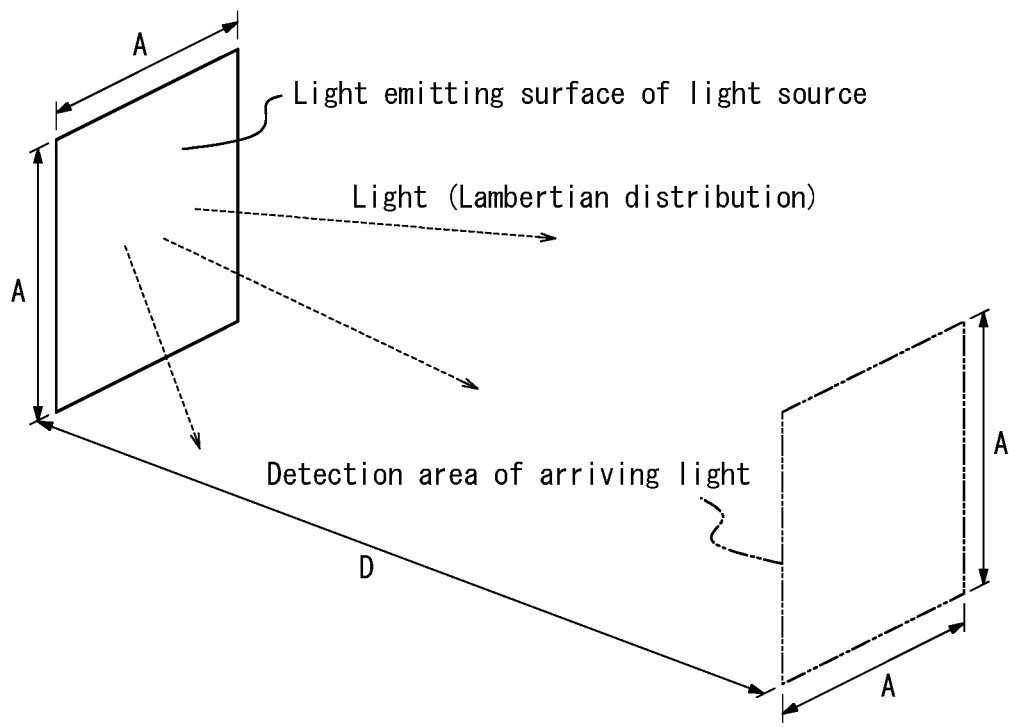
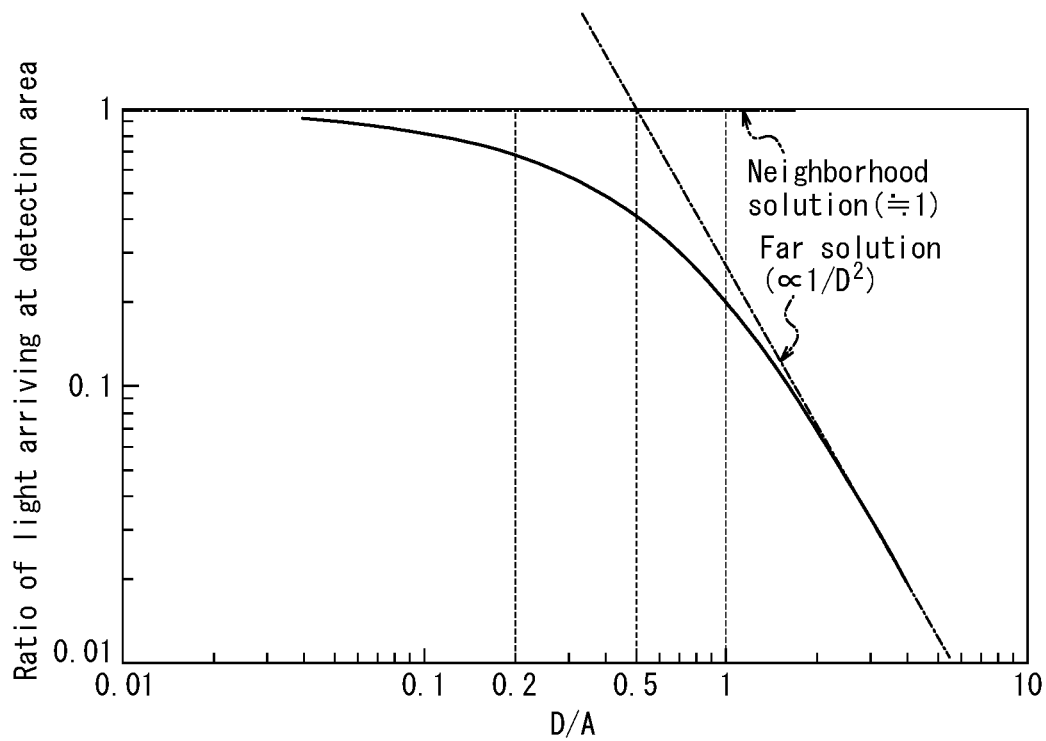

OPTICAL CHEMICAL ANALYSIS APPARATUS

CROSS-REFERENCE TO RELATED APPLICATIONS

The present application claims priority to Japanese Patent Application No. 2020-160120 (filed on Sep. 24, 2020), the content of which is incorporated herein by reference in its entirety.

TECHNICAL FIELD

The present disclosure relates to an optical chemical analysis apparatus.

BACKGROUND

When the refractive index of a material forming a structure, such as a thin film formed by crystals or the like, is greater than the refractive index of material outside the structure, light propagating through the structure travels while repeatedly undergoing total internal reflection at the interface with the outside of the structure. When light propagating through the structure undergoes total reflection at this interface, it extends outside, where the refractive index is smaller. This extension is referred to as an evanescent wave (see FIG. 9). The evanescent wave EW may be absorbed by a substance 52 adjacent to the structure 51 while the light L propagates. Therefore, the substance 52 in contact with the structure 51 can be detected, identified, or the like from the change in intensity of the light L propagating through the structure 51. An analytical method using the above-described principle of evanescent waves EW is referred to as the attenuated total reflection (ATR) method and is used to analyze the chemical composition and concentration, for example, of the substance 52. Infrared light is typically used as the propagated light. Substances have the property of selectively absorbing infrared light of particular wavelengths. Analysis or sensing of a substance can therefore be performed by propagating infrared light that matches the absorption spectrum of the substance to be measured.

Patent literature (PTL) 1 proposes an optical waveguide sensor in which the ATR method is applied to a sensor. This optical waveguide sensor has a core layer formed on a substrate, allows light to pass through the core layer, and uses the evanescent wave to detect a substance in contact with the core layer.

In a sensor using the ATR method, it is necessary to have a point where light from the light source is introduced into the core layer of the optical waveguide and a point where the light is extracted from the core layer of the optical waveguide toward a photodetector. Therefore, a diffraction grating is often installed between the light source and the optical waveguide, and between the photodetector and the optical waveguide, to bend the optical axis of the light. Typically, coherent light with high directivity, such as laser light, is irradiated onto the diffraction grating to introduce light into the core layer. The less light is lost at the diffraction grating during this process, the greater the intensity of the signal detected by the photodetector becomes, increasing the sensitivity of the sensor.

CITATION LIST

Patent Literature

PTL 1: JP 2005-300212 A

SUMMARY

Incoherent light sources with low directivity, such as LEDs and heaters, are increasingly used as light sources for devices using optical waveguides. These light sources often have a relatively large light emitting area of 100 μm×100 μm or more. Technology for efficiently introducing such incoherent light with low directivity into the core layer of the optical waveguide is needed.

It would be helpful to provide an optical chemical analysis apparatus capable of coupling incoherent light emitted from a light source with an optical waveguide in a highly efficient manner.

An optical chemical analysis apparatus according to an embodiment of the present disclosure includes:

an optical waveguide with a core layer that includes a light propagator, through which light can propagate in an extension direction of the light propagator, and a diffraction grating that connects optically to the light propagator; and a light source configured to inject the light into the diffraction grating by emitting incoherent light, wherein the diffraction grating further includes at least one light intake region for introduction of light from the light source, and the light source includes at least one light emitting point at a position such that a difference between a shortest optical distance Lab to the light intake region and a longest optical distance Lac to the light intake region is less than half of a wavelength, in a vacuum, of the light.

An optical chemical analysis apparatus according to an embodiment of the present disclosure includes:

an optical waveguide with a core layer that includes a light propagator, through which light can propagate in an extension direction of the light propagator, and a diffraction grating that connects optically to the light propagator; and a light source configured to inject the light into the diffraction grating by emitting incoherent light, wherein the diffraction grating further includes at least one light intake region for introduction of light from the light source, the diffraction grating includes a plurality of connected portions that connect optically to the light propagator, and the light source includes at least one light emitting point at a position such that a difference between an optical distance Lam to a point M of the diffraction grating that is a midpoint of a line segment connecting any two connected portions among the plurality of connected portions in plan view and an optical distance Lai to a closer one of the two connected portions is less than half of a wavelength, in a vacuum, of the light.

An optical chemical analysis apparatus according to an embodiment of the present disclosure includes:

an optical waveguide with a core layer that includes a light propagator, through which light can propagate in an extension direction of the light propagator, and a diffraction grating that connects optically to the light propagator; and a light source configured to inject the light into the diffraction grating by emitting incoherent light, wherein the diffraction grating further includes at least one light intake region for introduction of light from the light source, and the light source includes at least one light emitting point at a position such that an area of the light intake region satisfying $|\sin(\Delta P)| < 0.1$ is 50% or more of a total area of the light intake region, where a phase difference $\Delta P$ is a product of a difference $\Delta L$ and a wave number, in a vacuum, of the light ($2\pi$/wavelength in a vacuum), and the difference $\Delta L$ is a difference between a shortest optical distance Lab to the light intake region and an optical distance Lad to a certain point in the light intake region.

The present disclosure can provide an optical chemical analysis apparatus capable of coupling incoherent light emitted from a light source with an optical waveguide in a highly efficient manner.

BRIEF DESCRIPTION OF THE DRAWINGS

In the accompanying drawings:

FIG. 3 is a diagram illustrating the relationship between a light source and a diffraction grating in an optical chemical analysis apparatus according to a first embodiment;

FIGS. 4A and 4B are diagrams illustrating the relationship between a light source and a diffraction grating in an optical chemical analysis apparatus according to a second embodiment;

FIG. 6 is a diagram illustrating the relationship between a light source and a diffraction grating in an optical chemical analysis apparatus according to a fourth embodiment;

FIG. 8 is a diagram illustrating proximity arrangement; and

DETAILED DESCRIPTION

Figure 1:
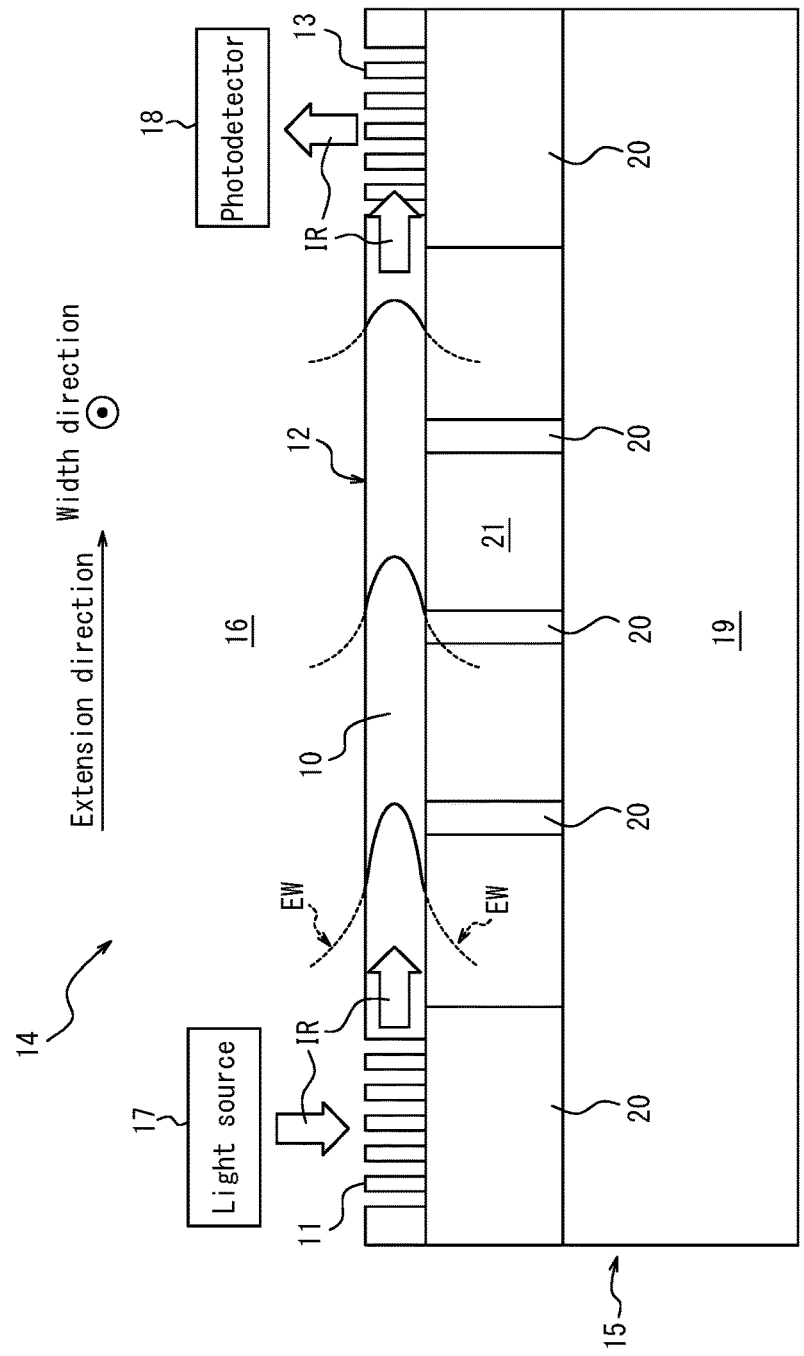
FIG. 1 is a diagram schematically illustrating a configuration of an optical chemical analysis apparatus of the present disclosure.

Embodiments of the present disclosure are now described, but the following embodiments do not limit the claimed subject matter. Furthermore, not all combinations of features described in the embodiments are necessarily essential to the solution to the problem of the present disclosure.

An optical chemical analysis apparatus according to an embodiment of the present disclosure includes an optical waveguide with a core layer that includes a light propagator, through which light can propagate in an extension direction of the light propagator, and a diffraction grating that connects optically to the light propagator. The optical chemical analysis apparatus also includes a light source configured to inject the light into the diffraction grating by emitting incoherent light. The diffraction grating further includes at least one light intake region for introduction of light from the light source, and the light source includes a light emitting point at a position such that the difference between the shortest optical distance Lab to the light intake region and the longest optical distance Lac to the light intake region is less than half of the wavelength, in a vacuum, of the light. In the present disclosure, the aforementioned diffraction grating is referred to as a first diffraction grating, which is distinguished from a second diffraction grating (diffraction grating for outputting light to a photodetector), described below.

In the optical chemical analysis apparatus according to the present embodiment, the light source includes a light emitting point at a position such that the difference between the shortest optical distance Lab to the light intake region and the longest optical distance Lac to the light intake region is less than half of the wavelength, in a vacuum, of the light. Consequently, the optical chemical analysis apparatus according to the present embodiment can couple incoherent light emitted from the light source with the optical waveguide in a highly efficient manner. Specifically, when the light emitted from one light emitting point of the light source spreads out concentrically and reaches each point of the light intake region of the first diffraction grating, even the light emitted from the incoherent light source can be regarded as being in phase in the light intake region if the difference in the optical distance to each point is less than half the wavelength of the light. Since light is taken into the core layer in the light intake region by interference between the wavelength of the light and the period of the structure forming the light intake region, the light intake region takes in the light arriving at the light intake region in units that can be regarded as being in phase in the light intake region. As a result of the light source including a light emitting point at a position such that the difference between the shortest optical distance Lab to the light intake region and the longest optical distance Lac to the light intake region is less than half of the wavelength, in a vacuum, of the light, the light emitted from this light emitting point will couple with the optical waveguide in a single mode throughout the light intake region. This enables highly efficient coupling of incoherent light with the optical waveguide. The optical distance Lac is the shortest optical distance from the light emitting point to the point on the light intake region that is optically farthest from the light emitting point.

The principle behind the present disclosure is now described in greater detail. The light emitted from an incoherent light source contains light with many different phases, even if only a single wavelength is extracted. However, even with an incoherent light source, the phases are aligned in the light wavefront formed by light that originates from the same point at the same time. In other words, even with incoherent light, the first diffraction grating (light intake region) operates for each component with aligned phase, and the components with aligned phase can be taken into the core layer as one propagation mode. Light originating from the same point at the same time spreads out with the in-phase plane as a concentric sphere. The surface of the light intake region is typically not spherical, but rather planar and uneven. The light arriving at the light intake region is therefore out of phase on the surface of the light intake region. A slight phase shift that does not result in reverse phase (the difference in optical distance being less than half the wavelength of the light) can be treated as in-phase. If the area of the light intake region is large, however, the light cannot be regarded as in-phase at all positions in the light intake region, and a plurality of in-phase groups are formed in the light intake region. Accordingly, if the area of the light intake region is large, a plurality of propagation modes end up forming for light that originates from the same point at the same time. On the other hand, to propagate light with a plurality of propagation modes in the light propagator, the cross-sectional area (width and height) of the light propagator perpendicular to the extension direction must have a size corresponding to the number of propagation modes. However, the cross-sectional area of the light propagator is typically very small. In the case of the first diffraction grating having a light intake region with a large area, the light propagator cannot propagate light in all of the propagation modes generated in the first diffraction grating. The number of in-phase groups formed in the light intake region of the first diffraction grating is therefore preferably equal to or less than the number of propagation modes in which light can be propagated in the light propagator. To propagate light efficiently in the light propagator, the light propagator is preferably a single-mode optical waveguide that propagates light in a single mode. Based on these considerations, the first diffraction grating is preferably configured so that when the light taken in by the first diffraction grating at one light intake region is guided to one light propagator, the number of in-phase groups formed in the light intake region is one. In other words, the first diffraction grating preferably includes a light intake region with a small area.

In the present embodiment, the light source preferably includes a light emitting point at a position such that the difference between the optical distance Lab and the optical distance Lac is less than one fourth of the wavelength, in a vacuum, of the light. When the light emitting point and the light intake region satisfy such a relationship, the light injected from the light source into the light intake region can be regarded as more in phase, and light can be efficiently taken into the core layer.

In the present embodiment, the light source preferably includes a light emitting point at a position such that the difference between the optical distance Lab and the optical distance Lac is less than 2.13 μm. For example, in an optical chemical analysis apparatus for analyzing $CO_2$, a representative gas present in the environment, infrared light with a central wavelength, in a vacuum, of approximately 4.26 μm is typically used as the light propagating through the core layer. In this case, half of the wavelength, in a vacuum, of the light is 2.13 μm.

In the present embodiment, half or more of the light emitting points of the light source are preferably arranged at positions such that the difference between the optical distance Lab and the optical distance Lac is less than half of the wavelength, in a vacuum, of the light, and all of the light emitting points of the light source are more preferably arranged at positions such that the difference between the optical distance Lab and the optical distance Lac is less than half of the wavelength, in a vacuum, of the light. When the light emitting points and the light intake region satisfy such a relationship, the light emitted from half or more of the light emitting points of the light source can be regarded as in phase at all of the points on the light intake region, and light can be efficiently taken into the core layer.

The first diffraction grating can include a plurality of light intake regions. In plan view, the external shape of the light source can be the smallest convex polygon covering all light emitting points. For example, the external shape of the light source can be a square or a rectangle as a convex polygon. The area of the smallest convex polygon (external shape) covering all light emitting points of the light source is preferably larger than the area of one light intake region in plan view, and light emitted from the light source is preferably taken in by a plurality of light intake regions.

When the light emitting area of the light source is large (i.e., when the area of the convex polygon covering all light emitting points is large), and the first diffraction grating includes a plurality of light intake regions, the light emitted from the light source is taken into the plurality of light intake regions, thereby enabling the optical chemical analysis apparatus to efficiently take the light emitted from the light source into the core layer.

The first diffraction grating can be configured so that a plurality of light intake regions are connected, without being individually distinguishable. In this case, the number of portions connected to the light propagator represents the substantial number of light intake regions, and the connected portions approximately indicate the end of the overall light intake region. The size of the first diffraction grating can therefore be specified using the connected portions.

In an embodiment, the light source includes a light emitting point at a position such that the difference between an optical distance Lam to a point M of the first diffraction grating that is the midpoint of a line segment connecting any two connected portions among the plurality of connected portions in plan view and an optical distance Lai to a closer one of the two connected portions is less than half of the wavelength, in a vacuum, of the light.

When the first diffraction grating is configured by a plurality of connected light intake regions, and such a relationship is satisfied, then for at least one light emitting point, the number of in-phase groups formed in the light intake region by the light emitted from the light emitting point becomes equal to or less than the number of connected portions. Therefore, all of the in-phase groups formed in the light intake region can be guided to the plurality of light propagators through the plurality of connected portions, and the optical chemical analysis apparatus can efficiently take the light emitted from the light source into the core layer.

In the present embodiment, the light source preferably includes a light emitting point at a position such that the difference between the optical distance Lam and the optical distance Lai is less than one fourth of the wavelength, in a vacuum, of the light. When the light emitting point and the light intake region satisfy such a relationship, the light injected from the light source into the light intake region can be regarded as more in phase, and light can be efficiently taken into the core layer.

In the present embodiment, the light source preferably includes a light emitting point at a position such that the difference between the optical distance Lam and the optical distance Lai is less than 2.13 μm. For example, in an optical chemical analysis apparatus for analyzing $CO_2$, a representative gas present in the environment, infrared light with a central wavelength, in a vacuum, of approximately 4.26 μm is typically used as the light propagating through the core layer. In this case, half of the wavelength, in a vacuum, of the light is 2.13 μm.

In the present embodiment, half or more of the light emitting points of the light source preferably satisfy the condition of being arranged at positions such that the difference between the optical distance Lam and the optical distance Lai is less than half of the wavelength, in a vacuum, of the light, and all of the light emitting points of the light source more preferably satisfy the condition of being arranged at positions such that the difference between the optical distance Lam and the optical distance Lai is less than half of the wavelength, in a vacuum, of the light. When the light emitting points and the light intake region satisfy such a relationship, the light emitted from half or more of the light emitting points of the light source can be regarded as in phase at all of the points on the light intake region, and light can be efficiently taken into the core layer.

As mentioned above, the light reaching the light intake region of the first diffraction grating from the light emitting point of the light source can be treated as being in phase if there is a small phase shift. Instead of the difference in optical distance, the phase shift can be used to determine the relationship between the light emitting point of the light source and the light intake region of the first diffraction grating.

In an embodiment, the light source includes at least one light emitting point such that the area of the light intake region satisfying $|\sin(\Delta P)|<0.1$ is 50% or more of the total area of the light intake region, where a phase difference $\Delta P$ is the product of a difference ΔL and the wave number, in a vacuum, of the light (2π/wavelength in a vacuum), and the difference ΔL is the difference between the shortest optical distance Lab to the light intake region and the optical distance Lad to a certain point in the light intake region.

When this relationship for the phase of light is satisfied, then for at least at one light emitting point, much of the light incident from that light emitting point onto the entire light intake region can be regarded as being in phase. The optical chemical analysis apparatus can therefore efficiently take the light emitted from the light source into the core layer. Here, if the wavelength in a vacuum is $\lambda_0$, the phase difference ΔP is expressed as "$\Delta L \times 2\pi/\lambda_0$". The value of 0.1 on the right-hand side indicates that the phase difference ΔP is within a very small range. In optics, when θ is small, the approximation sin θ≈θ is often used in discussion. The aforementioned case is in a range such that the approximation |sin(ΔP)|≈ΔP can be used.

Each constituent element of the optical chemical analysis apparatus will be described below with specific examples.

<Optical Waveguide>

The optical waveguide is an optical waveguide used in an optical chemical analysis apparatus that analyzes the chemical composition and concentration of a substance to be measured (gas, liquid, or the like). The optical waveguide is provided with a core layer that includes a light propagator, through which light can propagate in the extension direction of the light propagator, and a first diffraction grating that receives light from a light source and guides the light to the light propagator. The optical waveguide is also provided with a substrate.

Here, the extension direction is a direction extending along at least one direction. For example, in a three-dimensional structure, a path that is the shortest distance from one end to the other end (or from any point to any other point) while touching the three-dimensional structure is an extension direction. Alternatively, the direction going from one end to the other end (or from any point to any other point) with the smallest change in cross-sectional area is also an extension direction. The extension direction includes not only straight directions but also curved directions.

For the first diffraction grating to guide light to the light propagator (i.e., for light to be introduced into the light propagator from the first diffraction grating), and for the light propagator to guide light to the second diffraction grating as described below (i.e., for light to be introduced into the second diffraction grating from the light propagator), the form of connection between the light intake region of the first diffraction grating, the light extraction region of the second diffraction grating, and the light propagator is not limited, provided that light can propagate between these components. For example, besides the case of these components being the same material (and in an identical crystal state) connected continuously without interruption, the case of optical connection between these components is also included. Examples of the components being optically continuous include the case of being optically continuous by virtue of being positioned coaxially, even if the components are discontinuous due to being formed by different materials (including the same element in different crystal states), and the case of being coupled by evanescent waves, for example as with a directional coupler, even if the components are discontinuous (with interruptions between components) due to not being coaxial. A directional coupler refers to an optical coupling state in which the direction of travel of light does not change before and after the transition of light from one side to the other using evanescent waves. In the present description, the state in which light can be guided and introduced between the first and second diffraction gratings and the light propagator is also referred to simply as the first and second diffraction gratings being connected with the light propagator.

The first diffraction grating is arranged opposite from and in close proximity to the light emitting surface of the light source. The first diffraction grating has one or more light intake regions, and the light intake regions receive light emitted from the light source. The light emitting surface of the light source is the portion, on the surface of the light source from which light is emitted, that is in contact with the substance to be measured. The proximity arrangement will be described later.

The optical waveguide is preferably further provided with a second diffraction grating into which light from the light propagator is introduced and which outputs light to a photodetector, and the second diffraction grating preferably has at least one light extraction region.

<<Core Layer>>

The core layer includes the light propagator, through which light can propagate in the extension direction of the light propagator, and the first diffraction grating that receives light from the light source and guides the light to the light propagator. The core layer can further include the second diffraction grating into which light from the light propagator is introduced and which outputs light to the photodetector.

The material of the core layer is not limited. Examples include core layers including single crystal silicon and polycrystalline silicon, amorphous silicon, silicon nitride, silicon germanium, germanium, gallium arsenide, indium phosphorus, indium antimony, indium gallium arsenide, indium gallium phosphorus, indium fluoride, diamond, sapphire, lithium niobate, chalcogenide glass, or the like. The core layer may be a multilayer film instead of a single-layer film.

The first diffraction grating and the light propagator may be formed from different materials. In this case, the material forming the light propagator is preferably single crystal silicon, and the material forming the first diffraction grating preferably contains polycrystalline silicon or amorphous silicon. Silicon is the most common material, and such a configuration can reduce the propagation loss in the light propagator and easily improve the processing freedom of the first diffraction grating.

Furthermore, a cross-section perpendicular to the extension direction at any position along the extension direction of the core layer may, for example, have a shape such that the distance from the center to the outer surface of the core layer in the cross-section varies, such as a rectangle, or a shape such that the distance from the center to the outer surface of the core layer in the cross-section does not vary, i.e., a circle.

At least a portion of the core layer may be exposed or coated by a thin film. This enables a portion of the exposed or coated core layer to be in direct contact with the substance to be measured or to be in contact with the substance to be measured via the thin film, so that the evanescent wave interacts with the substance to be measured, thereby enabling analysis of the chemical composition and concentration of the substance to be measured. The coating is preferably thinner than ¼ of the wavelength, in a vacuum, of the light propagating through the core layer.

The light propagating through the core layer may be infrared light serving as an analog signal. Infrared light serving as an analog signal does not refer to determining the change in the energy of light to be one of two values, i.e. 0

(low level) or 1 (high level), but rather to a signal that carries the amount of change in the energy of light. This enables the optical waveguide to be applied to sensors and analyzers. The wavelength, in a vacuum, of the infrared light may be at least 2 μm and less than 12 μm in this case. This is the wavelength band that is absorbed by gases typically present in the environment ($CO_2$, CO, NO, $N_2O$, $SO_2$, $CH_4$, $H_2O$, $C_2H_6O$, and the like). This enables use of the optical waveguide as a gas sensor.

The core layer may include curved portions. The aspect ratio of the contour of the core layer can thus be brought closer to 1 when the entire core layer is in plan view, enabling a reduction in size of the optical waveguide and the optical chemical analysis apparatus.

<<<Light Propagator>>>

The light received by the first diffraction grating is introduced into the light propagator, which propagates and guides the light to the second diffraction grating. The light propagator refers to a portion of the core layer through which light can propagate in the extension direction of the light propagator. This portion has a width in the width direction perpendicular to the extension direction, and the width does not change along the extension direction. A cross-section perpendicular to the extension direction at any position along the extension direction of the light propagator may, for example, have a shape such that the distance from the center to the outer surface of the core layer in the cross-section varies, such as a rectangle, or a shape such that the distance from the center to the outer surface of the core layer in the cross-section does not vary, i.e., a circle.

The light propagator can have a uniform thickness (i.e., height of the light propagator) in the extension direction. A uniform thickness means, for example, a difference of 200 nm or less in the thickness (height).

To propagate light efficiently, the light propagator is preferably a single mode optical waveguide that propagates light in a single mode. That is, in at least a portion of the light propagator, the light propagator preferably has a width or height (thickness) such that light propagates in a single mode, and more preferably has a width and height such that light propagates in a single mode. In other words, the light propagator preferably has a cross-sectional area where light propagates in a single mode in a cross-section perpendicular to the extension direction.

The width or height of at least a portion of the light propagator is preferably smaller than 1 μm, and the cross-sectional area of the surface perpendicular to the extension direction of at least a portion of the light propagator is preferably smaller than 1 $\mu m^2$. The width or height smaller than 1 μm and the cross-sectional area smaller than 1 $\mu m^2$ are the dimensions of the light propagator that enable propagation in a single mode, or a mode number near a single mode, for the light emitted from the light source in the present embodiment (infrared light with a wavelength, in a vacuum, of at least 2 μm and less than 12 μm).

<<<First Diffraction Grating, Second Diffraction Grating>>>

The first diffraction grating receives light from the light source and guides the light to the light propagator. The first diffraction grating has one or more light intake regions, and at least one of the light intake regions receives light emitted from the light source. The core layer can include the second diffraction grating. The second diffraction grating has at least one light extraction region into which light is introduced from the light propagator and which outputs the light to a photodetector.

The light intake region and the light extraction region may be portions of the surface where an unevenness is formed with a specific period (or a plurality of periods). In a cross-sectional view of the optical waveguide in a plane that includes the unevenness or concave and convex portions, the depth of grooves in the concave portions of the unevenness may increase to separate the core layer. In such a configuration, the convex portions form discontinuous islands.

The light intake regions and light extraction regions can be provided in such a way that in plan view, the patterns of parallel unevenness extend in a straight line or an arc shape. The shape in which the unevenness extends can be freely chosen.

The first diffraction grating and second diffraction grating can have any appropriate shape in plan view, such as a shape having a section whose width increases from the connection side towards the end side, with the apex near the portion on the side where the first diffraction grating and second diffraction grating are connected to the light propagator. Specifically, in addition to a fan shape centered near the portion where the first diffraction grating and the second diffraction grating are connected to the light propagator, other acceptable shapes include a triangle (such as an isosceles triangle) centered near the connected portion where the first diffraction grating and the second diffraction grating are connected to the light propagator, and a shape having a section whose width increases from the portion connected to the light propagator towards the light intake region and the light extraction region, with the apex near the portion connected to the light propagator, and a section continuous with this section and having any shape, such as a rectangle. The shape of the light intake region and light extraction region is preferably linearly symmetrical with respect to any virtual line along the direction from the connection side to the end side.

As mentioned above, the light propagator refers to the portion of the core layer whose width does not change in the extension direction. The connected portion refers to the point of connection between the first diffraction grating or the second diffraction grating and the portion that extends with no change in width (light propagator). The first diffraction grating or the second diffraction grating can have a plurality of connected portions that optically connect with the light propagator.

Next, the wavelength dispersion (wavelength width of propagating light) of the light propagating through the optical chemical analysis apparatus is described. The optical chemical analysis apparatus analyzes the substance to be measured by propagating light that matches the absorption spectrum of the substance to be measured through the light propagator. Hence, in the first diffraction grating, light of approximately the same wavelength band as the absorption spectrum of the substance to be measured is preferably taken in. In general, the absorption wavelength range of light for a substance may have a width of approximately ±0.1 μm relative to the central wavelength and is never an exact single wavelength. For example, the typical absorption wavelength of $CO_2$, a gas present in the environment, is approximately 4.20 μm to 4.35 μm, with a width of 0.15 μm. In this case, narrowly selecting an exact single wavelength would leave out a wavelength region effective for analysis, which is not desirable in an optical chemical analysis apparatus. In particular, the optical chemical analysis apparatus in the present embodiment uses an incoherent light source such as an LED as the light source, and to effectively use light with a certain wavelength range (wavelength band) from the incoherent light source, the wavelength band selected in the first diffraction grating region also has a certain width (approximately ±0.1 relative to the central wavelength).

The width of the wavelength band selected in the first diffraction grating region can be explained using the uncertainty principle. When the first diffraction grating takes light from the light source into the core layer, it is not possible to distinguish which part of the light intake region the light struck. In other words, when the one-dimensional size of the light intake region is $\Delta x$, the light has an indeterminacy of the position of $\Delta x$. Therefore, the indeterminacy $\Delta p$ of the momentum p can be represented by Expression (2) from the indeterminacy principle represented by Expression (1).

$$\Delta x \Delta p \geq \frac{h}{4\pi} \quad \text{Expression (1)}$$

$$\Delta p \geq \frac{h}{4\pi \Delta x} \quad \text{Expression (2)}$$

Here, h is Planck's constant ($6.626 \times 10^{-34}$ kgm²/s).

Since the wavelength of light, $\lambda$, can be represented by Expression (3), the uncertainty $\Delta \lambda$ of the wavelength can be represented by Expression (4).

$$\lambda = \frac{h}{p} \quad \text{Expression (3)}$$

$$\Delta \lambda = \frac{h}{p} - \frac{h}{p + \Delta p} \quad \text{Expression (4)}$$

Expression (5) is derived from Expression (2) and Expression (4). In other words, to provide for the indeterminacy $\Delta \lambda$ of the wavelength, the indeterminacy $\Delta x$ of the position needs to satisfy Expression (5).

$$\Delta x \geq \frac{h(h - \Delta \lambda p)}{4\pi \Delta \lambda p^2} \quad \text{Expression (5)}$$

Assuming that the wavelength dispersion suitable for the optical chemical analysis apparatus is 0.1 μm, it suffices for the uncertainty $\Delta \lambda$ of the wavelength in the light intake region to be 0.1 μm. Expression (6) is derived by substituting $\Delta \lambda = 0.1$ into Expression (5).

$$\Delta x \geq \frac{h(h - 0.1p)}{0.4\pi p^2} \quad \text{Expression (6)}$$

The one-dimensional size of the light intake region is $\Delta x$, and the area S thereof is $\Delta x^2$. It thus follows that when the area S of the light intake region satisfies Expression (7), the wavelength of light taken in at the light intake region can be provided with a dispersion of approximately 0.1 μm. In other words, the area S of the light intake region preferably satisfies Expression (7).

$$S \geq \left(\frac{h(h - 0.1p)}{0.4\pi p^2}\right)^2 \quad \text{Expression (7)}$$

When $CO_2$ is analyzed using the optical chemical analysis apparatus, and the average wavelength, in a vacuum, of the light propagating through the core layer is 4.26 μm, then using Expression (3) to calculate Expression (6) and Expression (7) indicates that the relationships $\Delta x \geq 14.1$ μm and $S \geq 198.9$ μm² should be satisfied.

The lower limit on the difference between the optical distance Lab and the optical distance Lac, and the difference between the optical distance Lam and the optical distance Lai, in the present embodiment can be calculated uniquely from the lower limit on the size of the light intake region indicated by Expression (6) or Expression (7). Therefore, only the lower limit on the size of the light intake region is specified.

The structure of the second diffraction grating can be the same as the structure of the first diffraction grating or may be a modification to the structure of the first diffraction grating. A modification to the structure of the first diffraction grating refers to the shape, configuration, arrangement, and the like of the second diffraction grating being a rotated form, enlarged form, reduced form, translated form, linearly symmetric form, or point symmetric form with respect to the shape, configuration, arrangement, and the like of the first diffraction grating. By adopting a structure for the second diffraction grating that is the same as the structure of the first diffraction grating, or a structure that is a modification to the structure of the first diffraction grating, the wavelength selectivity of the first diffraction grating and the wavelength selectivity of the second diffraction grating can be made substantially equal. This can avoid the light loss that occurs when the wavelength selectivity differs between the first diffraction grating and the second diffraction grating.

<<Substrate>>

The substrate is not limited as long as the core layer can be formed on the substrate. A support layer, described below, can also be formed on the substrate. Specific examples of the substrate include a silicon substrate and a GaAs substrate.

<<Support Layer>>

A support layer is optionally provided. The support layer connects at least a portion of the substrate to at least a portion of the core layer. The support layer is not limited, as long as the support layer is capable of joining the substrate and the core layer. The support layer is preferably a material that has a smaller refractive index than the core layer, with respect to light of any wavelength or light propagating through the core layer. Examples of the material forming the support layer include $SiO_2$. The support layer is not an essential component in the present disclosure. The core layer may be joined to the substrate by the support layer, or the core layer may be formed directly on the substrate. The support layer may be partially present, and at least a portion of the core layer may be floating without being bonded to the support layer. In other words, a space may be formed between the substrate and the core layer except in a region where the support layer is provided in an optical waveguide configured in this way. By core layer having a floating portion, the amount of interaction between the evanescent wave and the substance to be measured can be increased, thereby improving the sensor sensitivity.

An example of a method of forming the support layer is to etch a buried oxide (BOX) layer ($SiO_2$ layer) of a silicon on insulator (SOI) substrate, thereby forming a structure in which the BOX layer supports the core layer (Si layer) with respect to the substrate (Si layer).

<Light Source>

The light source may be any light source capable of injecting light into the core layer. An incandescent bulb, a ceramic heater, a micro electro mechanical systems (MEMS) heater, an infrared light emitting diode (LED), or the like can be used as the light source in the case of using infrared light to analyze a gas. In other words, the light source can be an incoherent light source. The light source can be arranged in any way that allows optical connection to the optical waveguide. For example, the light source may be arranged adjacent to the optical waveguide in the same unit as the optical waveguide or may be arranged at a certain distance from the optical waveguide as a separate unit. A mercury lamp, an ultraviolet LED, or the like can be used as the light source in the case of using ultraviolet light to analyze a gas. The light source has a light-emitting surface with an area of 100 µm×100 µm or more, for example.

In one embodiment, the light source may include a light emitting layer with a plurality of light emitting points and a highly refractive material layer to refract light from the light emitting layer and guide the light into the light intake region. The highly refractive material layer is partially in contact with the substance to be measured and is positioned between the light emitting layer and the substance to be measured. Here, the plurality of light emitting points are each a light emitting body that emits light. In the light emitting layer, the plurality of light emitting bodies are arranged at equal intervals in a direction perpendicular to the stacking direction, for example, but this configuration is not limiting. The highly refractive material layer is, for example, formed from Si (silicon) and GaAs (gallium arsenide), but this configuration is not limiting. For example, the light source is an LED formed on one of the main surfaces of the GaAs substrate. The light emitting points are in the light emitting layer of the LED, and the light emitted by the LED from the light emitting layer may be emitted from the other main surface opposite the one main surface of the GaAs substrate. In this case, the GaAs substrate becomes the highly refractive material layer. The highly refractive material is not limited as long as it can refract the light from the light emitting layer and guide the light to the core layer (light intake region), but the highly refractive material preferably has a higher refractive index than that of the light emitting layer. The refractive index is also preferably higher than that of the gas to be measured. The provision of the highly refractive material layer makes it easier to include a light emitting point at a position such that the difference between the optical distance Lab and the optical distance Lac is less than half the wavelength, in a vacuum, of the light. Similarly, it becomes easier to include a light emitting point at a position such that the difference between the optical distance Lam and the optical distance Lai is less than half the wavelength, in a vacuum, of the light. Similarly, it becomes easier to include a light emitting point at a position such that the area of the light intake region satisfying $|\sin(\Delta P)|<0.1$ is 50% or more of the total area of the light intake region with regard to the difference $\Delta L$, between the optical distance Lab and the optical distance Lad, and the phase difference $\Delta P$.

The light propagating through the core layer of the optical waveguide provided in the optical chemical analysis apparatus may be infrared light serving as an analog signal. Infrared light serving as an analog signal does not refer to determining the change in the energy of light to be one of two values, i.e. 0 (low level) or 1 (high level), but rather to a signal that carries the amount of change in the energy of light. The wavelength, in a vacuum, of the infrared light may be at least 2 µm and less than 12 µm. This is the wavelength band that is absorbed by gases typically present in the environment ($CO_2$, $CO$, $NO$, $N_2O$, $SO_2$, $CH_4$, $H_2O$, $C_2H_6O$, and the like). An optical chemical analysis apparatus for analyzing these gases can thereby be achieved.

The light emitting surface of the light source can be arranged opposite from and in close proximity to the first diffraction grating. Consequently, a larger proportion of the light outputted from the light source towards the first diffraction grating can reach the first diffraction grating (the three-dimensional angle created by the first diffraction grating becomes wider when the first diffraction grating is viewed from the light source), enabling efficient introduction of light into the optical waveguide.

Here, proximity refers to a length of 1 mm or less or $\sqrt{Ss}$ or less, preferably 500 µm or less or $0.5 \times \sqrt{Ss}$ or less, and more preferably 200 µm or less or $0.2 \times \sqrt{Ss}$ or less, where Ss is the area of the light emitting surface of the light source. The length refers to the length measured along the thickness direction from the lower edge of the light emitting surface of the light source on the optical waveguide side to the first diffraction grating located closest to the light emitting surface of the light source in the thickness direction (height direction) of the optical waveguide. Other members, such as lenses or optical fibers, are preferably not present between the light emitting surface of the light source and the first diffraction grating, and the light outputted from the light emitting surface preferably directly reaches the first diffraction grating through a small space. An inexpensive optical chemical analysis apparatus can thereby be achieved.

<Photodetector>

The photodetector may be any photodetector capable of detecting light that has propagated through the core layer of the optical waveguide. A thermal infrared sensor such as a pyroelectric sensor, a thermopile, or a bolometer; a quantum infrared sensor such as a diode or a phototransistor; or the like can be used as the photodetector in the case of using infrared light for gas analysis. A quantum ultraviolet sensor, such as a diode or a phototransistor, or the like can be used in the case of using ultraviolet light for gas analysis.

The photodetector can be arranged opposite from and in close proximity to the second diffraction grating. In other words, the second diffraction grating can be arranged opposite from and in close proximity to the photodetector. Consequently, a larger proportion of the light outputted from the second diffraction grating toward the photodetector can reach the photodetector (the three-dimensional angle created by the photodetector becomes wider when the photodetector is viewed from the second diffraction grating), enabling efficient introduction of light into the photodetector. Proximity may also refer here to the length described in the proximity arrangement between the light source and the first diffraction grating. Other members, such as lenses or optical fibers, are preferably not present between the second diffraction grating and the photodetector, and the light outputted from the second diffraction grating preferably directly reaches the photodetector through a small space. An inexpensive optical chemical analysis apparatus can thereby be achieved.

First Embodiment

FIG. 1 is a diagram illustrating the schematic configuration of an optical chemical analysis apparatus 14 according to a first embodiment and is also a conceptual drawing of the ATR method using an optical waveguide 15. As illustrated in FIG. 1, the optical chemical analysis apparatus 14 is installed and used in an external space 16 containing a gas to be analyzed (including detection). The gas to be measured is air, for example, and the gases contained in the air are to be analyzed. The optical chemical analysis apparatus 14 includes the optical waveguide 15, a light source 17 capable of injecting light into a core layer 12 provided in the optical waveguide 15, and a photodetector 18 capable of detecting light propagated through the core layer 12. In the present embodiment, the light is infrared rays IR.

In more detail, the optical chemical analysis apparatus 14 is obtained by manufacturing the optical waveguide 15, and as illustrated in FIG. 1, by subsequently installing the light source 17 so that infrared rays IR can be injected into the first diffraction grating 11 (for example, a grating coupler) of the optical waveguide 15, and arranging the photodetector 18 to be capable of detecting infrared rays IR exiting from the second diffraction grating 13 (for example, a grating coupler) of the optical waveguide 15.

The optical waveguide 15 includes a substrate 19, the core layer 12 through which the infrared rays IR can propagate, and a support layer 20 configured to connect at least a portion of the substrate 19 with at least a portion of the core layer 12 and to support the core layer 12 with respect to the substrate 19. The core layer 12 and the substrate 19 are, for example, formed from silicon (Si). The support layer 20 is formed from silicon dioxide ($SiO_2$), for example. The substrate 19 and the support layer 20 have a plate shape, for example. The support layer 20 may support at least a portion of the core layer 12 or may support all of the core layer 12. In the example in FIG. 1, the support layer 20 supports all of the first diffraction grating 11 and the second diffraction grating 13 and a portion of the light propagator 10 discontinuously in the extension direction. Consequently, the optical waveguide 15 has a void 21 with no predetermined layer, such as a cladding layer, between the light propagator 10 and the substrate 19, except in the region where the light propagator 10 is discontinuously connected to the support layer 20 in the extension direction and where the support layer 20 is provided.

The core layer 12 includes the first diffraction grating 11 formed at one end in the extension direction and the second diffraction grating 13 formed at the other end. The core layer 12 includes the light propagator 10 between the first diffraction grating 11 and the second diffraction grating 13, which are at respective ends in the extension direction. The thickness of the light propagator 10 may be uniform in the optical waveguide 15. In addition, the width of the light propagator 10 may be uniform in the optical waveguide 15. The width direction is the direction perpendicular to the extension direction and the thickness direction. The thickness direction is a direction parallel to the stacking direction in which the substrate 19, the support layer 20, and the core layer 12 are stacked.

The first diffraction grating 11 is arranged in the output direction of the light source 17. The optical waveguide 15 is installed so that the main surface of the substrate 19 is perpendicular to the vertical direction (stacking direction). The main surface of the substrate 19 is a surface perpendicular to the thickness direction of the substrate 19. In other words, the main surface is the surface with the greatest area among the six surfaces forming the substrate 19. That is, the output direction of the light source 17 is vertically below the light source 17 when the optical waveguide 15 is installed in this way. The first diffraction grating 11 couples the infrared rays IR injected from the light source 17 into the core layer 12. Therefore, the light propagating through the core layer 12 is inputted from the thickness direction of the first diffraction grating 11. The second diffraction grating 13 is arranged in the direction opposite the photodetector 18. The direction opposite the photodetector 18 is vertically below the photodetector 18 when the optical waveguide 15 is installed as described above. The second diffraction grating 13 is configured to extract the infrared rays IR propagating through the core layer 12 and emit the infrared rays IR toward the photodetector 18. Therefore, the light propagating through the core layer 12 is outputted in the thickness direction of the second diffraction grating 13.

In this way, the portion of the core layer 12 arranged on the light source 17 side (light injection side) includes the first diffraction grating 11. The portion of the core layer 12 arranged on the photodetector 18 side (light output side) includes the second diffraction grating 13. In addition, the core layer 12 includes the light propagator 10, from the center to both ends in the extension direction, through which infrared IR injected from the first diffraction grating 11 propagates to be emitted from the second diffraction grating 13. The evanescent wave EW that extends out from the core layer 12 is mainly absorbed by the substance to be measured that is present in the external space 16 around the light propagator 10.

In the optical chemical analysis apparatus 14, the first diffraction grating 11 is arranged opposite from and in close proximity to the light emitting surface of the light source 17. Specifically, the length measured along the thickness direction from the lower edge of the light emitting surface of the light source 17 on the optical waveguide 15 side to the first diffraction grating 11 located closest to the light emitting surface of the light source 17 in the thickness direction of the optical waveguide 15 is 1 mm or less, or $\sqrt{Ss}$ or less relative to the area Ss of the light emitting surface of the light source 17. The length is preferably 500 µm or less or $0.5\times\sqrt{Ss}$ or less, and more preferably 200 µm or less or $0.2\times\sqrt{Ss}$ or less. By the length thus being 1 mm or less or $\sqrt{Ss}$ or less, a larger proportion of the light outputted from the light source 17 towards the first diffraction grating 11 can reach the first diffraction grating 11 (the three-dimensional angle created by the first diffraction grating 11 becomes wider when the first diffraction grating 11 is viewed from the light source 17), enabling efficient introduction of light into the optical waveguide 15. The effects of the aforementioned length similarly hold for the second diffraction grating 13 and the light receiving surface of the photodetector 18, enabling efficient introduction of light into the photodetector 18.

From the above perspective, no lower limit is placed on the length, and it is acceptable for the light emitting surface of the light source 17 and the first diffraction grating 11 to be in contact with each other. However, from the viewpoint of properly manufacturing the optical chemical analysis apparatus 14, the length is preferably 3 µm or more. Lenses, optical fibers, and the like are not present between the light emitting surface of the light source 17 and the first diffraction grating 11, and the light outputted from the light emitting surface directly reaches the first diffraction grating 11 through a space with a short length. The optical chemical analysis apparatus 14 can thereby be achieved inexpensively.

Here, FIG. 8 illustrates the numerical calculation results of the arrival rate of light when the length of the proximity arrangement is varied by optical simulation. FIG. 8 illustrates the proportion of light emitted from the light emitting surface of the light source that reaches the first diffraction grating 11 as a function of D/A, assuming that the shape of the light emitting surface of a Lambertian light source is a square with a side length of A, and the length of the proximity arrangement is D. Since the length of the square is A, the area of the light emitting surface is A squared. It is assumed that the area of the first diffraction grating 11, which receives the light emitted from the light source, is the same as the area of the light emitting surface of the light source. As illustrated in FIG. 8, in the region where D/A>1 (i.e., when the light source is arranged at a long distance, so that D>A), the proportion of light reaching the first diffraction grating 11 is approximated by the inverse square law with respect to the length D. This is because at a long distance, the projected area created by the light that reaches the first diffraction grating 11 increases in proportion to the square of the length D, and the irradiance diminishes accordingly. On the other hand, in the region where D/A<1 (i.e., when the light source is arranged nearby, so that D<A), the proportion of the arriving light exhibits a tendency to saturate at the maximum value as D/A is smaller. In other words, by setting the length D to less than A (the square root of the area of the light emitting surface), preferably less than 0.5 A, and more preferably less than 0.2 A, light can be efficiently introduced into the optical waveguide 15. This principle similarly holds for the second diffraction grating 13 and the light receiving surface of the photodetector 18. In this case, the area of the second diffraction grating 13 corresponds to the aforementioned area of the light emitting surface of the light source, and the area of the optical detection surface of the photodetector 18 corresponds to the aforementioned area of the first diffraction grating 11. The area of the light emitting surface of the light source and the area of the optical detection surface of the photodetector 18 may have a size of 1 mm$^2$ or larger.

In the optical chemical analysis apparatus 14, the light source 17 injects infrared light with a wavelength of at least 2 μm and less than 12 μm into the core layer 12. By injecting the aforementioned infrared rays into the core layer 12, the evanescent wave EW extending from the core layer 12 is absorbed by the substance to be measured in the external space 16, such as $CO_2$, CO, NO, $N_2O$, $SO_2$, $CH_4$, $H_2O$, $C_2H_6O$, or another gas, and the substance to be measured can be analyzed.

Figure 2A:
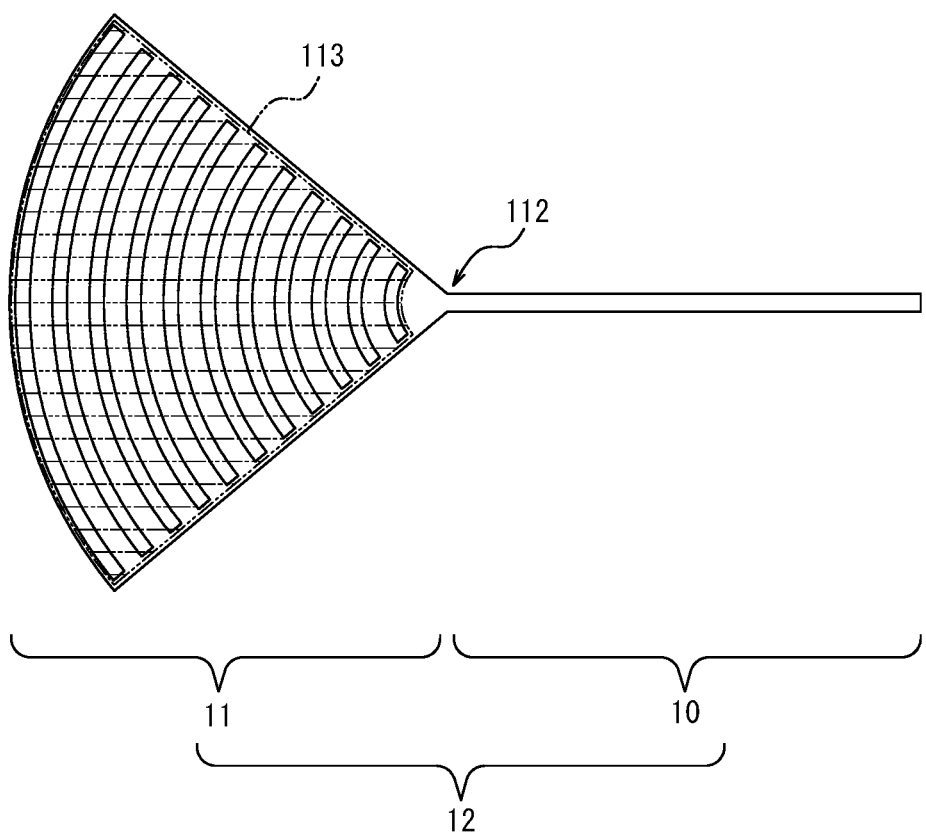
FIGS. 2A and 2B are diagrams illustrating the peripheral structure of a first diffraction grating.
Figure 2B:
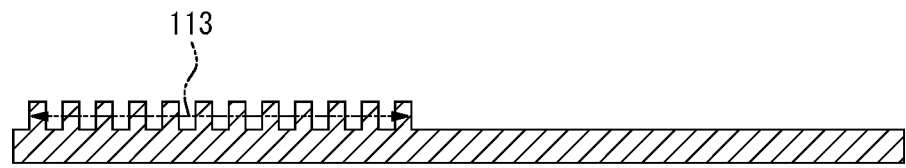

FIGS. 2A and 2B are diagrams illustrating the peripheral structure of the first diffraction grating 11. FIG. 2A is a plan view of the peripheral structure of the first diffraction grating 11. FIG. 2B is a cross-sectional view of the peripheral structure of the first diffraction grating 11. The core layer 12 includes a light propagator 10 that has a propagation path through which light can propagate in the extension direction of the light propagator 10, and a first diffraction grating 11 that receives light from a light source 17 and guides the light to the light propagator 10. As illustrated in FIG. 2A, the first diffraction grating 11 has a light intake region 113 for introducing light from the light source 17. In the present embodiment, the first diffraction grating 11 has a shape (fan shape) whose width increases from the connection side towards the end side, with the apex near the connected portion 112. The connected portion 112 refers to the point of connection between the first diffraction grating 11 and the portion that extends with no change in width (light propagator 10), as described above.

FIG. 3 is a cross-sectional view illustrating the relationship between the light source 17 and the first diffraction grating 11 of the optical chemical analysis apparatus 14 according to the present embodiment. The light source 17 is an LED formed on one of the main surfaces of the substrate. The light emitting point 171 is in the light emitting layer 172 of the LED, and the light emitted from the light emitting layer 172 of the LED is emitted from the other main surface opposite the one main surface of the substrate after passing through the highly refractive material layer 173.

As illustrated in FIG. 3, point A is the position of one light emitting point 171. Points B and C are the two positions of the light intake region 113 where the light emitted from the one light emitting point 171 (i.e., point A) arrives. The distance along the path of the light from point A to point B is the optical distance Lab. The distances along the path of the light from point A to point C are the optical distance Lac and the optical distance Lac'. Here, point B is located directly below point A. In other words, the optical distance Lab is the shortest optical distance from point A to the light intake region 113. In addition, point C is located at the end of the light intake region 113 farther from point A. In other words, the optical distance Lac is the longest optical distance from point A to the light intake region 113. Here, the optical distance Lac' passes through a circuitous path on the way from point A to point C and is not the shortest optical distance connecting the two points. Therefore, in the optical chemical analysis apparatus 14 according to the present embodiment, the optical distance Lac' is excluded from the longest optical distance from point A to the light intake region 113.

In the present embodiment, the light source 17 includes a light emitting point 171 at a position such that the difference between the shortest optical distance Lab to the light intake region 113 and the longest optical distance Lac to the light intake region 113 is less than half of the wavelength, in a vacuum, of the light. In other words, in the case of including the light emitting point 171 at a position such that the difference between the optical distance Lab and the optical distance Lac is less than half of the wavelength, in a vacuum, of the light, then for at least one light emitting point 171, the light injected from the light emitting point 171 into the entire light intake region 113 can be regarded as being in phase. Light can thereby efficiently be taken into the core layer 12.

In the present embodiment, the light source 17 preferably includes a light emitting point 171 at a position such that the difference between the optical distance Lab and the optical distance Lac is less than one fourth of the wavelength, in a vacuum, of the light, so that light from the light source 17 can be taken into the core layer 12 even more efficiently. The light source 17 preferably includes a light emitting point 171 at a position such that the difference between the optical distance Lab and the optical distance Lac is less than 2.13 μm. Furthermore, more than half of the light emitting points 171 of the light source 17 are preferably at positions such that the difference between the optical distance Lab and the optical distance Lac is less than half the wavelength, in a vacuum, of the light.

Second Embodiment

FIGS. 4A and 4B are diagrams illustrating the relationship between the light source 17 and the first diffraction grating 11 in the optical chemical analysis apparatus 14 according to a second embodiment. In the present embodiment, the first diffraction grating 11 includes a plurality (four in the example in FIG. 4A) of light intake regions 113. The remaining configuration of the optical chemical analysis apparatus 14 is the same as in the first embodiment. In FIGS. 4A and 4B, the same reference signs are attached to the same elements as in FIGS. 1 to 3, and a description thereof is omitted to avoid redundant explanations.

In plan view, the external shape of the light source 17 can be the smallest convex polygon covering the light emitting points 171. Convex polygons include, for example, triangles, squares, and octagons. In the present embodiment, the external shape of the light source 17 is rectangular. In the present embodiment, the first diffraction grating 11 has a plurality of light intake regions 113, and the area of the rectangle that is the external shape of the light source 17 is larger than the area of one light intake region 113 in plan view, so that light emitted from the light source 17 is taken into the plurality of light intake regions 113 (four light intake regions 113).

When the light emitting area of the light source 17 is large (i.e., the area of the convex polygon covering the light emitting point 171 is large), the optical chemical analysis apparatus 14 can efficiently take in the light emitted from the light source 17 into the core layer 12 by the first diffraction grating 11 including a plurality of light intake regions 113 and the light emitted from the light source 17 being taken into the plurality of light intake regions 113.

Third Embodiment

Figure 5A:
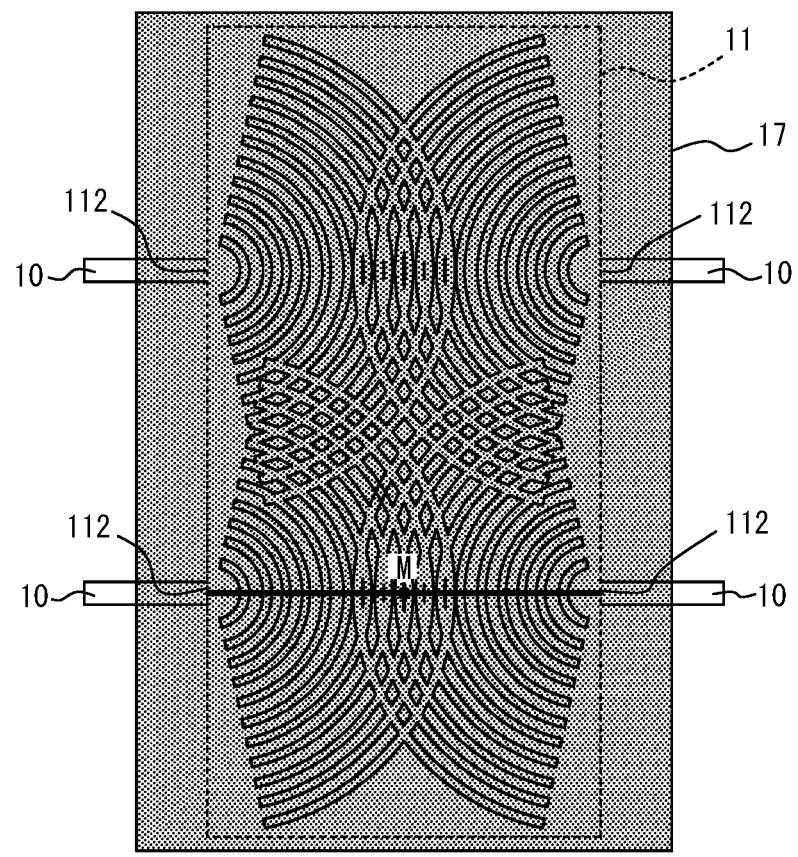
FIGS. 5A and 5B are diagrams illustrating the relationship between a light source and a diffraction grating in an optical chemical analysis apparatus according to a third embodiment.
Figure 5B:
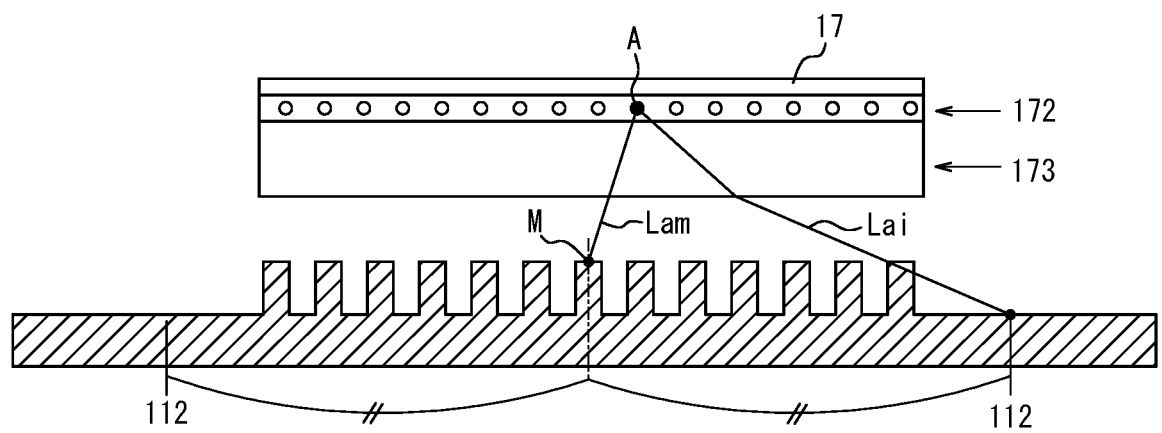

FIGS. 5A and 5B are diagrams illustrating the relationship between the light source 17 and the first diffraction grating 11 in the optical chemical analysis apparatus 14 according to a third embodiment. In the present embodiment, the first diffraction grating 11 includes a plurality (four in the example in FIG. 5A) of connected light intake regions 113. The remaining configuration of the optical chemical analysis apparatus 14 is the same as in the first embodiment. In FIGS. 5A and 5B, the same reference signs are attached to the same elements as in FIGS. 1 to 3, and a description thereof is omitted to avoid redundant explanations.

In the first diffraction grating 11, the plurality of light intake regions 113 are connected, and the light intake regions 113 cannot be individually distinguished. The number of connected portions 112 connected to the light propagator 10 represents the substantial number of light intake regions 113, and the connected portions 112 approximately indicate the end of the overall light intake region 113. The size of the first diffraction grating 11 can therefore be defined using the connected portions 112.

In the example in FIG. 5A, point M of the first diffraction grating 11 indicates the midpoint of a line segment connecting the two lower connected portions 112. As illustrated in FIG. 5B, point A is the position of one light emitting point 171. The distance along the path of the light from point A to point M is the optical distance Lam. In the example in FIG. 5B, the distance along the path of the light from point A to the closer right-side connected portion 112 is the optical distance Lai. In the present embodiment, the light source 17 includes a light emitting point 171 at a position such that the difference between the optical distance Lam to the point M of the first diffraction grating 11 that is the midpoint of a line segment connecting any two connected portions 112 among the plurality of connected portions 112 in plan view and the optical distance Lai to the closer one of the two connected portions 112 is less than half of the wavelength, in a vacuum, of the light. When the first diffraction grating 11 is configured by a plurality of connected light intake regions 113, and such a relationship is satisfied, then for at least one light emitting point 171, the number of in-phase groups formed in the light intake region 113 by the light emitted from the light emitting point 171 becomes equal to or less than the number of connected portions 112. Therefore, all of the in-phase groups formed in the light intake region 113 can be guided to the plurality of light propagators through the plurality of connected portions 112, and the optical chemical analysis apparatus 14 can efficiently take the light emitted from the light source 17 into the core layer 12.

The light source 17 preferably includes a light emitting point 171 at a position such that the difference between the optical distance Lam and the optical distance Lai is less than one fourth of the wavelength, in a vacuum, of the light, so that light from the light source 17 can be taken into the core layer 12 even more efficiently. The light source 17 preferably includes a light emitting point 171 at a position such that the difference between the optical distance Lam and the optical distance Lai is less than 2.13 µm. Furthermore, more than half of the light emitting points 171 of the light source 17 are preferably at positions such that the difference between the optical distance Lam and the optical distance Lai is less than half the wavelength, in a vacuum, of the light.

Fourth Embodiment

FIG. 6 is a diagram illustrating the relationship between the light source 17 and the first diffraction grating 11 of the optical chemical analysis apparatus 14 according to a fourth embodiment. The configuration of the optical chemical analysis apparatus 14 is the same as in the first embodiment. In FIG. 6, the same reference signs are attached to the same elements as in FIGS. 1 to 3, and a description thereof is omitted to avoid redundant explanations.

The light reaching the light intake region 113 of the first diffraction grating 11 from the light emitting point 171 of the light source 17 can be treated as being in phase if there is a small phase shift. The efficiency of capturing light into the core layer 12 differs depending on whether the light emitted from the light emitting point 171 can be treated as being in phase. In the present embodiment, instead of the difference in optical distance, the phase shift is used to determine the relationship between the light emitting point 171 of the light source 17 and the light intake region 113 of the first diffraction grating 11.

In FIG. 6, point A is the position of one light emitting point 171. Point B and point D are the two positions of the light intake region 113 where the light emitted from the one light emitting point 171 (i.e., point A) arrives. The distance along the path of the light from point A to point B is the optical distance Lab. The distance along the path of the light from point A to point D is the optical distance Lad. As in the first embodiment, the optical distance Lab is the shortest optical distance from point A to the light intake region 113. The optical distance Lad is an optical distance that differs from the optical distance Lab (i.e. that is not the shortest optical distance).

In the present embodiment, the light source 17 includes a light emitting point 171 such that the area of the light intake region 113 satisfying $|\sin(\Delta P)|<0.1$ is 50% or more of the total area of the light intake region 113, where a phase difference $\Delta P$ is calculated as the product of a difference $\Delta L$ and the wave number, in a vacuum, of the light ($2\pi$/wavelength in a vacuum), and the difference $\Delta L$ is the difference between the shortest optical distance Lab to the light intake region 113 and the optical distance Lad to a certain point in the light intake region 113. When this relationship for the phase of light is satisfied, then for at least at one light emitting point 171, much of the light incident from that light emitting point 171 onto the entire light intake region 113 can be regarded as being in phase. The optical chemical analysis apparatus 14 can therefore efficiently take the light emitted from the light source 17 into the core layer 12. Here, if the wavelength in a vacuum is $\lambda_0$, the phase difference $\Delta P$ is expressed as "$\Delta L \times 2\pi/\lambda_0$".

Next, the preferred propagation mode is described with reference to FIG. 7. In the present embodiment, the light source 17 is an incoherent light source. The light emitted from an incoherent light source includes light of many different phases. However, even with an incoherent light source, the phases are aligned in the light wavefront formed by light that originates from the same point (such as the same light emitting point 171) of the light source 17 at the same time. In other words, even with incoherent light, the first diffraction grating 11 (light intake region 113) operates for each component with aligned phase, and the components with aligned phase can be taken into the core layer 12 as one propagation mode. Light originating from the same point at the same time spreads out with the in-phase plane as a concentric sphere. Here, since the surface of the light intake region 113 is not a sphere but a flat surface with unevenness, the light arriving at the light intake region 113 is out of phase on the surface of the light intake region 113.

Figure 7:
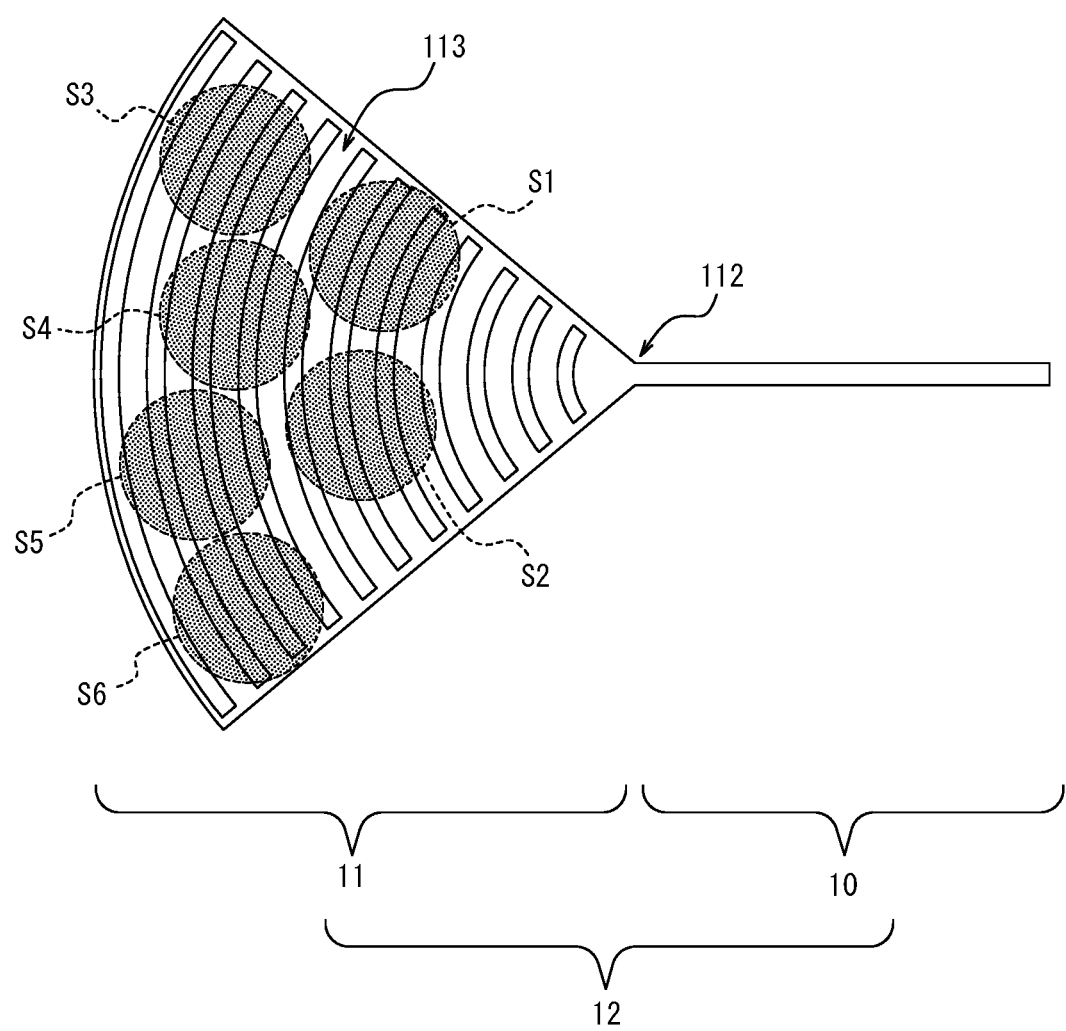
FIG. 7 is a diagram illustrating a transmission mode.
Figure 9:
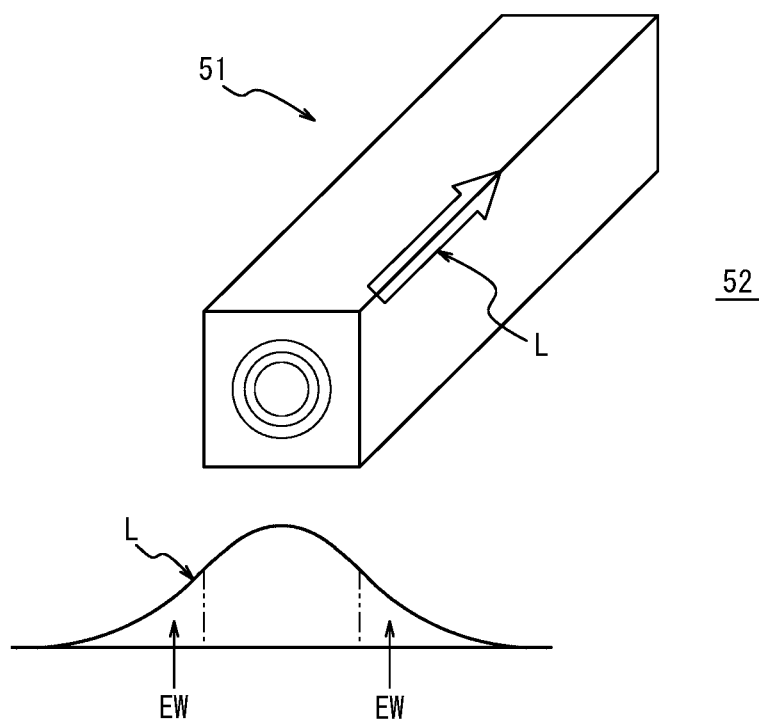
FIG. 9 is a diagram illustrating an evanescent wave of light propagating through an optical waveguide.

As illustrated in FIG. 7, when the area of the light intake region 113 of the first diffraction grating 11 is large, a plurality of in-phase groups (S1 to S6) are formed inside the light intake region 113. Accordingly, if the light intake region 113 is large, a plurality of propagation modes end up forming for light that originates from the same point at the same time. To propagate light with a plurality of propagation modes in the light propagator 10, the cross-sectional area (width and height) of the light propagator 10 perpendicular to the extension direction must have a size corresponding to the number of propagation modes. Therefore, a light propagator 10 with a very small cross-sectional area, such as the one in the present embodiment, cannot propagate light in all of the propagation modes occurring in the first diffraction grating 11. Furthermore, to propagate light efficiently, the light propagator 10 is preferably a single mode optical waveguide that propagates light in a single mode. Based on these considerations, the first diffraction grating 11 is preferably configured so that when the light taken in by the first diffraction grating 11 at one light intake region 113 is guided to one light propagator 10, the number of in-phase groups formed in the light intake region 113 is one. In other words, the first diffraction grating 11 is preferably provided with a light intake region 113 of such a size that the number of propagation modes formed in the light intake region 113 becomes one. The light propagator 10 also preferably has a cross-sectional area such that light propagates in a single mode.

For light from the light source 17 to be taken into the core layer 12 more efficiently and efficiently propagated, the light propagator 10 preferably has a width in the width direction perpendicular to the extension direction of the light propagator 10 and a height in the height direction perpendicular to the extension direction and the width direction, and at least a portion of the light propagator 10 preferably has a width or a height at which the light from the light source 17 propagates in a single mode in the width direction and/or the height direction. At least a portion of the light propagator 10 may have both a width and height at which the light propagates in a single mode in both the width direction and the height direction. The width or height of at least a portion of the light propagator 10 is preferably smaller than 1 µm. The cross-sectional area of a surface perpendicular to the extension direction of at least a portion of the light propagator 10 may be less than 1 µm². The width or height smaller than 1 µm and the cross-sectional area smaller than 1 µm² are the dimensions of the light propagator 10 that enable propagation in a single mode, or a mode number near a single mode, for the light emitted from the light source 17 in the present embodiment (infrared light with a wavelength, in a vacuum, of at least 2 µm and less than 12 µm).

The light propagator 10 has been described as preferably having a cross-sectional area that enables light to propagate in a single mode (or a mode number near a single mode). This is also true for the first through third embodiments.

Although embodiments of the present disclosure have been explained with reference to the accompanying drawings and examples, it is to be noted that various changes and modifications can be made by those of ordinary skill in the art based on the present disclosure. Furthermore, not all combinations of features described in the embodiments are necessarily essential to the solution to the problem of the present disclosure.

INDUSTRIAL APPLICABILITY

The present disclosure can provide an optical chemical analysis apparatus capable of coupling incoherent light emitted from a light source with an optical waveguide in a highly efficient manner.

The invention claimed is:

1. An optical chemical analysis apparatus comprising:
an optical waveguide with a core layer that includes a light propagator, through which light can propagate in an extension direction of the light propagator, and a diffraction grating that connects optically to the light propagator; and
a light source configured to inject the light into the diffraction grating by emitting incoherent light, wherein
the diffraction grating further includes at least one light intake region for introduction of light from the light source, and
the light source includes at least one light emitting point at a position such that a difference between a shortest optical distance Lab to the light intake region and a longest optical distance Lac to the light intake region is less than half of a wavelength, in a vacuum, of the light.

2. The optical chemical analysis apparatus of claim 1, wherein the light source includes a light emitting point at a position such that the difference between the optical distance Lab and the optical distance Lac is less than one fourth of the wavelength, in a vacuum, of the light.

3. The optical chemical analysis apparatus of claim 1, wherein the light source includes a light emitting point at a position such that the difference between the optical distance Lab and the optical distance Lac is less than 2.13 µm.

4. The optical chemical analysis apparatus of claim 1, wherein half or more of the at least one light emitting point of the light source are arranged at positions such that the difference between the optical distance Lab and the optical distance Lac is less than half of the wavelength, in a vacuum, of the light.

5. The optical chemical analysis apparatus of claim 1, wherein the at least one light intake region of the diffraction grating includes a plurality of light intake regions, an area of a smallest convex polygon covering all light emitting points of the light source is larger than an area of one light intake region among the plurality of light intake regions in plan view, and light emitted from the light source is taken in by the plurality of light intake regions.

6. An optical chemical analysis apparatus comprising:
an optical waveguide with a core layer that includes a light propagator, through which light can propagate in an extension direction of the light propagator, and a diffraction grating that connects optically to the light propagator; and a light source configured to inject the light into the diffraction grating by emitting incoherent light, wherein the diffraction grating further includes at least one light intake region for introduction of light from the light source, the diffraction grating includes a plurality of connected portions that connect optically to the light propagator, and the light source includes at least one light emitting point at a position such that a difference between an optical distance Lam to a point M, of the diffraction grating, that is a midpoint of a line segment connecting any two connected portions among the plurality of connected portions in plan view and an optical distance Lai to a closer one of the two connected portions is less than half of a wavelength, in a vacuum, of the light.

7. The optical chemical analysis apparatus of claim 6, wherein the light source includes a light emitting point at a position such that the difference between the optical distance Lam and the optical distance Lai is less than one fourth of the wavelength, in a vacuum, of the light.

8. The optical chemical analysis apparatus of claim 6, wherein the light source includes a light emitting point at a position such that the difference between the optical distance Lam and the optical distance Lai is less than 2.13 μm.

9. The optical chemical analysis apparatus of claim 6, wherein half or more of the at least one light emitting point of the light source are arranged at positions such that the difference between the optical distance Lam and the optical distance Lai is less than half of the wavelength, in a vacuum, of the light.

10. An optical chemical analysis apparatus comprising:
an optical waveguide with a core layer that includes a light propagator, through which light can propagate in an extension direction of the light propagator, and a diffraction grating that connects optically to the light propagator; and
a light source configured to inject the light into the diffraction grating by emitting incoherent light, wherein
the diffraction grating further includes at least one light intake region for introduction of light from the light source, and
the light source includes at least one light emitting point at a position such that an area of the light intake region satisfying $|\sin(\Delta P)|<0.1$ is 50% or more of a total area of the light intake region, where a phase difference $\Delta P$ is a product of a difference $\Delta L$ and a wave number, in a vacuum, of the light ($2\pi$/wavelength in a vacuum), and the difference $\Delta L$ is a difference between a shortest optical distance Lab to the light intake region and an optical distance Lad to a certain point in the light intake region.

11. The optical chemical analysis apparatus of claim 1, wherein an area S of the light intake region in plan view satisfies Expression (1), $$S \geq \left(\frac{h(h-0.1p)}{0.4\pi p^2}\right)^2 \qquad \text{Expression (1)}$$

where h is Planck's constant, and p is a momentum of light obtained by $p=h/\lambda$, with $\lambda$ being an average wavelength, in a vacuum, of light propagating through the core layer.

12. The optical chemical analysis apparatus of claim 1, wherein the light propagator has a width in a width direction orthogonal to the extension direction of the light propagator and a height in a height direction orthogonal to the extension direction and the width direction, and at least a portion of the light propagator has a width or a height at which the light propagates in a single mode in the width direction and/or the height direction.

13. The optical chemical analysis apparatus of claim 12, wherein a width or a height of at least a portion of the light propagator is less than 1 μm.

14. The optical chemical analysis apparatus of claim 12, wherein at least a portion of the light propagator has a width and a height at which the light propagates in a single mode in both the width direction and the height direction.

15. The optical chemical analysis apparatus of claim 12, wherein a cross-sectional area of a surface perpendicular to the extension direction of at least a portion of the light propagator is less than 1 μm².

16. The optical chemical analysis apparatus of claim 1, wherein the light source is an LED formed on one main surface of a substrate, the at least one light emitting point is inside a light emitting layer of the LED, and light emitted from the light emitting layer of the LED exits from another main surface opposite from the one main surface of the substrate.

17. The optical chemical analysis apparatus of claim 1, wherein the diffraction grating is arranged in close proximity to the light source.

18. The optical chemical analysis apparatus of claim 1, wherein the at least one light emitting point includes a plurality of light emitting points, and the light source comprises a light emitting layer including the plurality of light emitting points and a highly refractive material layer arranged between the light emitting layer and the light intake region to refract light from the light emitting layer and guide the light into the light intake region.

* * * * *